United States Patent [19]

Higuchi et al.

[11] Patent Number: 5,000,187
[45] Date of Patent: Mar. 19, 1991

[54] BLOOD PRESSURE MEASURING APPARATUS

[75] Inventors: Tomoe Higuchi, Aichi; Minoru Niwa, Nagoya, both of Japan

[73] Assignee: Colin Electronics Co., Ltd., Japan

[21] Appl. No.: 310,895

[22] Filed: Feb. 16, 1989

[30] Foreign Application Priority Data

Aug. 11, 1986 [JP] Japan .................. 61-188168

[51] Int. Cl.⁵ .............................................. A61B 5/02
[52] U.S. Cl. .................................. 128/681; 128/682; 128/677
[58] Field of Search .................. 128/672, 677–686

[56] References Cited

U.S. PATENT DOCUMENTS

| | | | |
|---|---|---|---|
| 4,625,277 | 11/1986 | Pearce et al. | 128/680 X |
| 4,754,761 | 7/1988 | Ramsey, III et al. | 128/683 |
| 4,774,960 | 10/1988 | Arnold et al. | 128/682 X |
| 4,777,959 | 10/1988 | Wallach et al. | 128/677 |

Primary Examiner—Max Hindenburg
Attorney, Agent, or Firm—Oliff & Berridge

[57] ABSTRACT

An apparatus for continuously measuring blood pressure of a subject based on magnitude variation of heartbeat-synchronous pulses produced from the subject, the apparatus including a detecting device for continuously detecting the pulses, the detecting device including an inflatable cuff to be set around a body portion of the subject, magnitude of the pulses being varied as pressure in the inflatable cuff is varied, the varying magnitude of the pulses being detected by the detecting device, a selecting device for selecting a pulse from the pulses detected at a preceding blood pressure measuring cycle, the selected pulse corresponding to maximum blood pressure determined at the preceding measuring cycle, a first determining device for determining a reference value based on at least a magnitude of the selected pulse, a second determining device for comparing, with the reference value, the varying magnitude of the heartbeat-synchronous pulses detected at a current blood pressure measuring cycle, and determining as temporary maximum blood pressure a pressure in the inflatable cuff when the varying magnitude of the currently detected pulses exceeds the reference value, and a display device for displaying the temporary blood pressure before determination of maximum blood pressure at the current blood pressure measuring cycle.

7 Claims, 4 Drawing Sheets

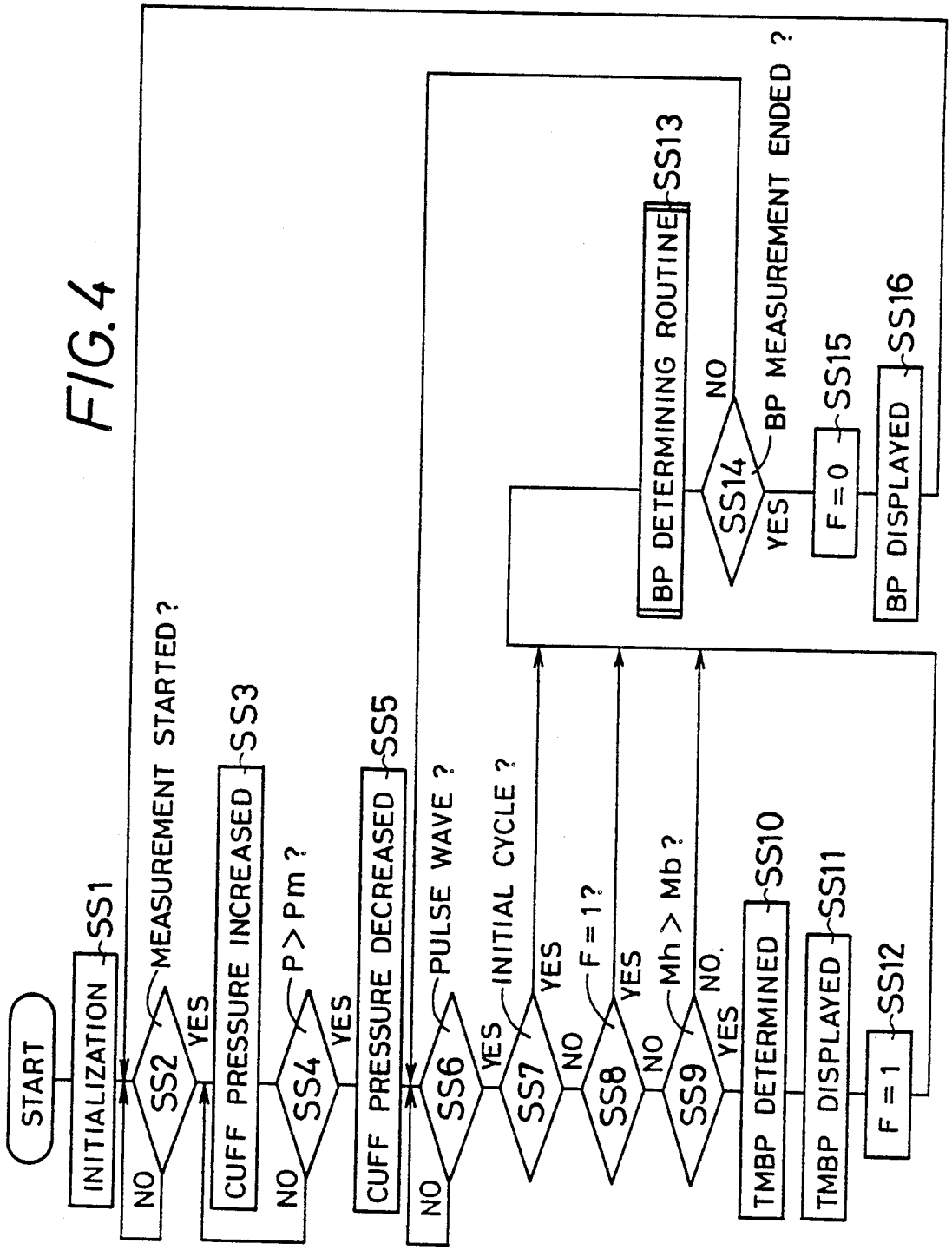

BLOOD PRESSURE MEASURING APPARATUS

BACKGROUND OF THE INVENTION

1. Field of the Invention

The present invention relates to a continuous-type blood pressure measuring apparatus, and particularly to such an apparatus which displays temporary maximum blood pressure before displaying proper and more accurate blood pressure at the end of each of continuous blood pressure measuring cycles.

2. Discussion of the Prior Art

There are known apparatus for continuously measuring blood pressure of a living body based on magnitude variation of heartbeat-synchronous pulses produced from the body. These apparatus include means for continuously detecting (a) Korotkoff sounds produced as pressure in an inflatable cuff set around a body portion of a subject is varied; (b) pulse wave (pressure oscillation) transmitted to an inflatable cuff; or (c) oscillation of the wall of an arterial vessel by utilizing Doppler effect. These apparatus are adapted to display maximum and minimum blood pressure at the end of each of continuous blood pressure measuring cycles. In other words, accurate blood pressure cannot be determined or displayed before a whole blood pressure measuring cycle is terminated, for example before pressure in an inflatable cuff whose level has been increased to a suitable upper level, is decreased to a suitable lower level. However, it is preferred that maximum blood pressure be displayed as temporary or estimated maximum blood pressure as early as possible prior to the end of each measuring cycle because the maximum blood pressure is more important information than other information concerning the blood pressure.

In the above background, it is proposed to determine temporary maximum blood pressure (hereinafter, referred to TMBP) at each of continuous blood pressure measuring cycles (hereinafter, referred to BPMC's) by selecting a pulse from heartbeat-synchronous pulses detected at a current BPMC which pulse corresponds to the TMBP, based on a maximum difference in magnitude between each pair of adjacent ones of the currently detected, consecutive heartbeat-synchronous pulses. In this case, however, the maximum difference, based on which the TMBP is determined, may be changed as the current BPMC is progressed. Consequently, TMBP, once displayed, may be changed to another TMBP in the course of detection of the following heartbeat-synchronous pulses during the current BPMC. Thus, the TMBP determined in the above-indicated manner is not reliable.

SUMMARY OF THE INVENTION

It is therefore an object of the present invention to provide a blood pressure measuring apparatus wherein more reliable temporary maximum blood pressure is determined and displayed at each of continuous blood pressure measuring cycles prior to the end of each cycle.

The above object has been achieved by the present invention, which provides a blood pressure measuring apparatus for continuously measuring blood pressure of a subject based on magnitude variation of heartbeat-synchronous pulses produced from the subject, the apparatus comprising: (a) detecting means for continuously detecting the heartbeat-synchronous pulses, the detecting means including an inflatable cuff to be set around a body portion of the subject, magnitude of the pulses being varied as pressure in the inflatable cuff is varied, the varying magnitude of the pulses being detected by the detecting means; (b) selecting means for selecting a pulse from the heartbeat-synchronous pulses detected at a preceding blood pressure measuring cycle, the selected pulse corresponding to maximum blood pressure determined at the preceding blood pressure measuring cycle; (c) first determining means for determining a reference value based on at least a magnitude of the selected pulse; (d) second determining means for comparing, with the reference value, the varying magnitude of the heartbeat-synchronous pulses detected at a current blood pressure measuring cycle, and determining as temporary maximum blood pressure a pressure in the inflatable cuff when the varying magnitude of the currently detected heartbeat-synchronous pulses exceeds the reference value; and (e) display means for displaying the temporary blood pressure before determination of maximum blood pressure at the current blood pressure measuring cycle.

In the blood pressure measuring apparatus constructed as described above, temporary maximum blood pressure (TMBP) of a subject at a current blood pressure measuring cycle (BPMC) is determined by comparing varying magnitude of heartbeat-synchronous pulses detected at the current BPMC, with a reference value determined based on at least a magnitude of a pulse of the heartbeat-synchronous pulses detected at the preceding BPMC which pulse corresponds to maximum blood pressure of the same subject at the preceding BPMC. Thus, the TMBP determined and displayed by the present apparatus is comparatively reliable. Furthermore, in the present apparatus, the TMBP is displayed upon detection of a pulse from the currently detected heartbeat-synchronous pulses which pulse corresponds to the TMBP, at each of continuous BPMC's except for an initial BPMC, before the termination of each BPMC, namely, before proper and more accurate maximum and minimum blood pressure is displayed. Thus, the TMBP displayed by the present apparatus is not changed during each measuring cycle, in contrast to the previously-indicated apparatus adapted to determine TMBP based on a maximum difference in magnitude between each pair of consecutive ones of heartbeat-synchronous pulses detected at a current BPMC.

In a preferred embodiment of the blood pressure measuring apparatus of the present invention, the first determining means determines the reference value by obtaining an average of magnitudes of three pulses of the heartbeat-synchronous pulses detected at the preceding blood pressure measuring cycle, the three pulses consisting of an intermediate pulse corresponding to the maximum blood pressure determined at the preceding blood pressure measuring cycle, and two pulses preceding and following the intermediate pulse.

In another embodiment of the apparatus of the invention, the first determining means determines the reference value based on the reference value determined at the preceding blood pressure measuring cycle and the reference value determined at a blood pressure measuring cycle preceding the preceding blood pressure measuring cycle.

In yet another embodiment of the apparatus of the invention, the heartbeat-synchronous pulses consist of pressure oscillations produced in the inflatable cuff synchronously with heartbeat of the subject.

In a further embodiment of the apparatus of the invention, the heartbeat-synchronous pulses consist of Korotkoff sounds produced from the body portion of the subject synchronously with heartbeat of the subject.

In another embodiment of the apparatus of the invention, the heartbeat-synchronous pulses are detected as the pressure in the inflatable cuff is decreased. Alternatively, the heartbeat-synchronous pulses may be detected as the pressure in the inflatable cuff is increased.

BRIEF DESCRIPTION OF THE DRAWINGS

The above and optional objects, features and advantages of the present invention will be better understood by reading the following detailed description of the presently preferred embodiment of the invention, when considered in connection with the accompanying drawings, in which:

FIG. 4 is a flow chart corresponding to FIG. 2, the flow chart illustrating operation of a modified blood pressure measuring apparatus of the invention.

DETAILED DESCRIPTION OF THE PREFERRED EMBODIMENT

Figure 1:
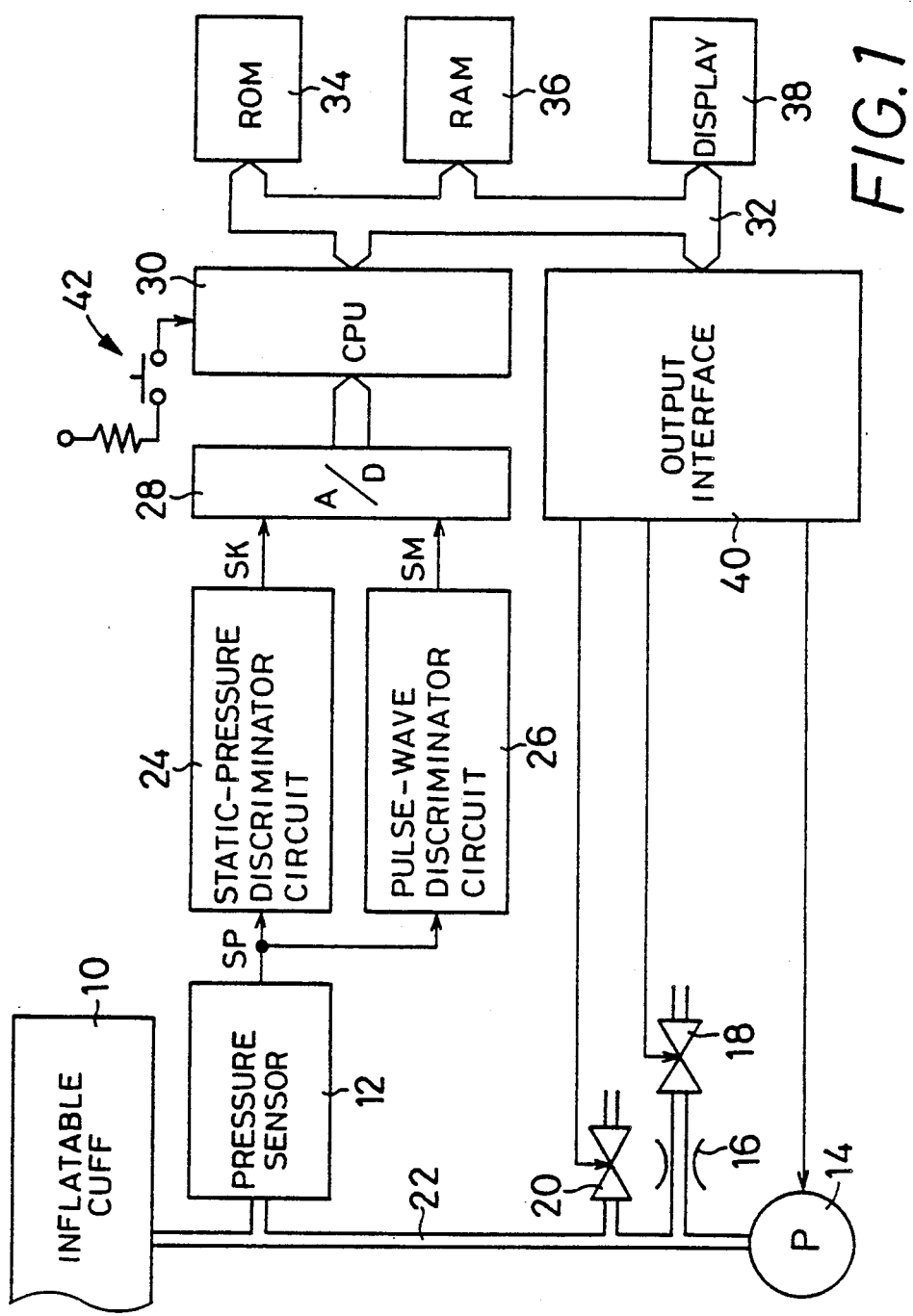
FIG. 1 is a diagrammatic view of a blood pressure measuring apparatus of the present invention.

Referring first to FIG. 1, there is shown a blood pressure measuring apparatus embodying the present invention. In the Figure, reference numeral 10 designates a bag-like rubber inflatable cuff to be set around an upper arm or the like of a subject. The inflatable cuff 10 is connected via piping 22 to a pressure sensor 12, an air pump 14, a slow-deflation restrictor 16, a slow-deflation electromagnetic valve 18, and a rapid-deflation electromagnetic valve 20. The pressure sensor 12 generates pressure signal SP representing pressure variation in the bag of the inflatable cuff 10, to a static-pressure discriminator circuit 24 and a pulse-wave discriminator circuit 26. The static pressure discriminator circuit 24 includes a low-pass filter (not shown) which separates, from pressure signal SP, cuff-pressure signal SK representing variation in static pressure in the inflatable cuff 10. Cuff-pressure signal SK is supplied to a CPU (central processing unit) 30 via an A/D (analog-to-digital) converter 28. The pulse wave discriminator circuit 26 includes a band-pass filter (not shown) which separates, from pressure signal SP, pulse-wave signal SM representing pulse wave. Pulse-wave signal SM is supplied to the CPU 30 via the A/D converter 28. The pulse wave consists of consecutive pulses produced from the subject synchronously with heartbeat of the subject, and is transmitted in the form of pressure oscillation to the inflatable cuff 10. In the present embodiment, the pulse wave corresponds to the heartbeat-synchronous pulses.

The CPU 30 is coupled via data bus 32 to a ROM (read only memory) 34, a RAM (random access memory) 36, a display 38, and an output interface 40. The CPU 30 processes the received signals according to programs pre-stored in the ROM 34 and by utilizing temporary-storage function of the RAM 36. While the CPU 30 controls the operation of each of the air pump 14 and electromagnetic valves 18, 20, the CPU 30 executes operations for blood pressure measurement. Specifically, the CPU 30 determines blood pressure based on cuff-pressure signal SK and pulse-wave signal SM, and commands the display 38 to display the determined blood pressure.

Figure 2:
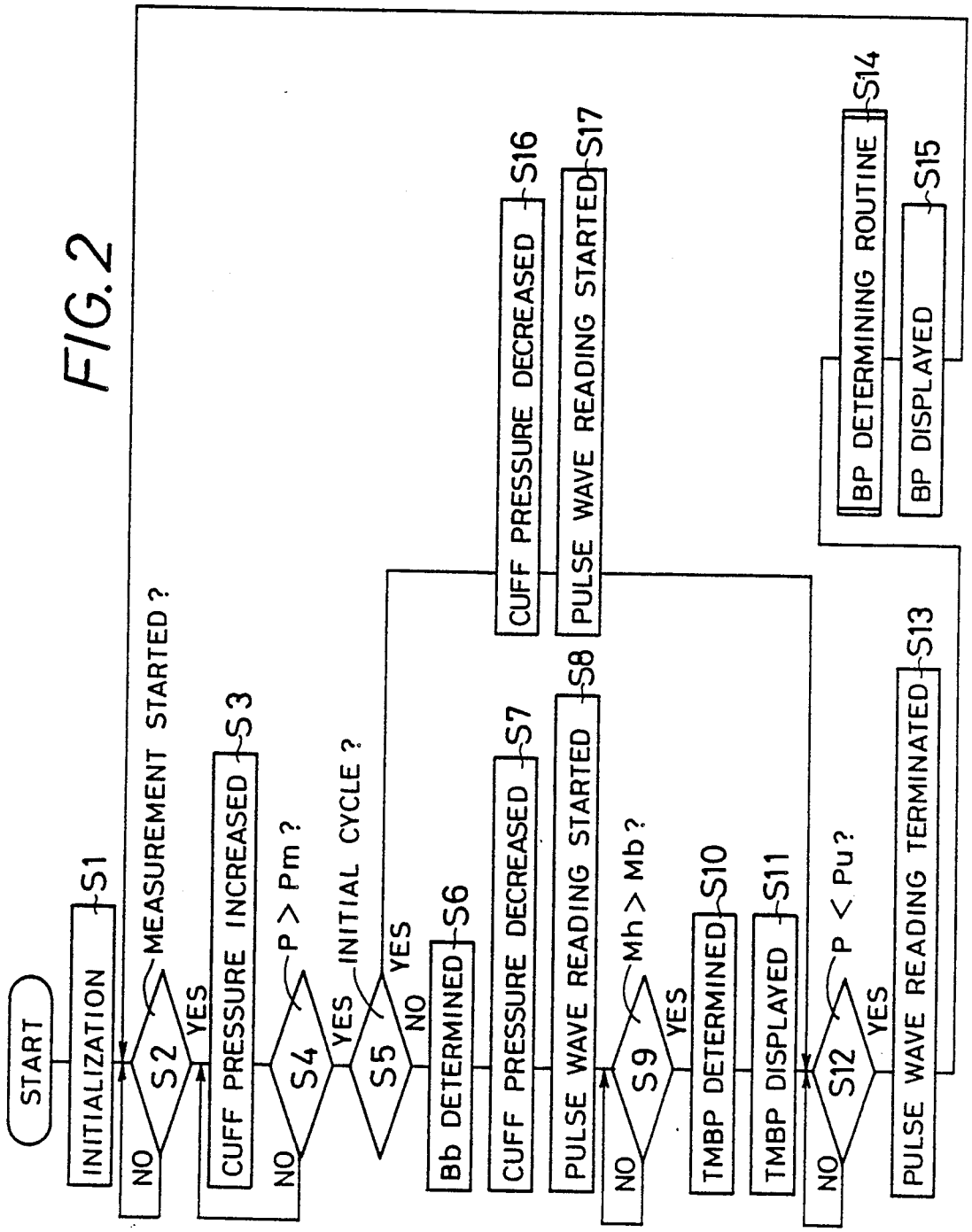
FIG. 2 is a flow chart illustrating operation of the apparatus of FIG. 1.

There will be described the operation of the present blood pressure measuring apparatus, in connection with the flow chart of FIG. 2.

Upon application of electric power to the present apparatus, the control of the CPU 30 goes to step S1 at which initialization is effected. Step S1 is followed by step S2 at which it is judged whether or not a START pushbutton switch 42 (FIG. 1) has been pushed. Alternatively, at step S2 it may be judged whether or not a timer of an activation circuit (not shown) has counted a predetermined time period. In either case, at step S2 it is judged whether or not blood pressure measurement has been started. If the judgement at step S2 is negative (NO), step S2 is repeated until the judgement is turned to be affirmative (YES). Once the judgement at step S2 is affirmative, step S2 is followed by step S3 at which both the electromagnetic valves 18, 20 are closed and the air pump 14 is activated, so as to inflate the cuff 10, namely, increase pressure in the cuff 10.

Figure 3:
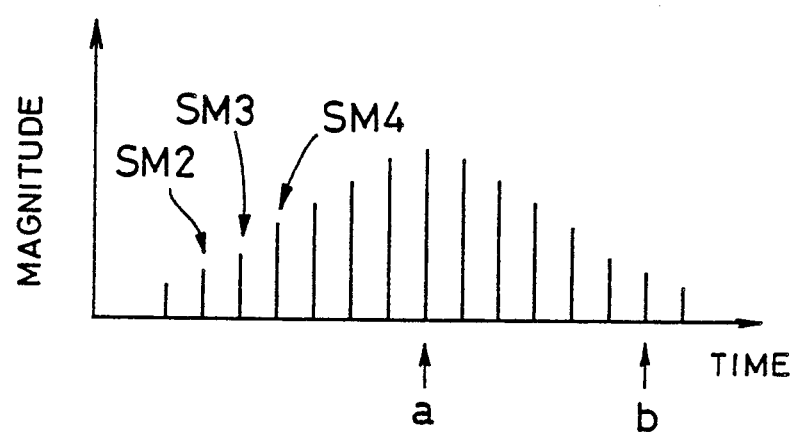
FIG. 3 is a graph showing pulses of pulse wave detected in a blood pressure measuring cycle.

At the following step S4 it is judged whether or not pressure level P in the cuff 10 has exceeded a predetermined target pressure level Pm. Pressure level Pm is predetermined to be sufficiently higher than maximum blood pressure of normal people or estimated maximum blood pressure of the subject, for example 180 mmHg. If cuff pressure P has not reached the target level Pm, steps S3 and S4 are repeated. Meanwhile, if cuff pressure P has exceeded the target Pm, step S4 is followed by step S5 at which it is judged whether or not a current blood pressure measuring cycle (BPMC) is an initial one. If the judgement at step S5 is negative, step S5 is followed by step S6 at which the CPU 30 determines a reference value Mb based on pulse wave signal SM detected at a BPMC preceding the current BPMC. The pulse wave signal SM detected at the preceding BPMC is represented by a plurality of pulses as shown in FIG. 3 which are obtained as a result of processing by the CPU 30. The reference value Mb is used for selecting a pulse from the pulses of pulse wave signal SM detected at the current BPMC which pulse corresponds to temporary maximum blood pressure (TMBP) for the current BPMC. More specifically described, in the case where the maximum blood pressure at the preceding BPMC is determined based on cuff pressure $P_{-1}$ corresponding to pulse SM3 of the pulses in the graph of FIG. 3, the reference value Mb is determined by calculating an average of magnitudes of three pulses consisting of pulse SM3 and two pulses SM2 and SM4 preceding and following pulse SM3. In the present embodiment, step S6 stored in the form of program in ROM 34, and the CPU 30 and RAM 36 for effecting step S6, cooperate with each other to serve as the means for selecting the pulse corresponding to the maximum blood pressure determined at the preceding BPMC, and also serve as the means for determining the reference value Mb.

Subsequently the control of the CPU 30 goes to step S7 at which the air pump 14 is stopped and the electromagnetic valve 18 is opened, so as to start slow deflation of the inflated cuff 10. Step S7 is followed by step S8 at which pulse wave signal SM supplied from the discriminator 26 at the current BPMC is processed into pulses like the pulse wave SM at the preceding BPMC shown in the graph of FIG. 3. As is clearly understood from FIG. 3, magnitude of the pulses of pulse wave signal SM is varied as cuff pressure P is slowly decreased. At the following step S9 it is judged whether or not the varying magnitude Mh of the pulses of the pulse wave signal SM detected at the current BPMC, has exceeded the reference value Mb determined at step S6. If the judgement at step S9 is negative, step S12 is repeated until the judgement is turned to be affirmative. Once the judgement at step S9 is affirmative, the control of the CPU 30 goes to step S10 at which the CPU 30 determines, as temporary maximum blood pressure for the current BPMC, a cuff pressure $P_0$ in the cuff 10 detected at the time of occurrence of a pulse of the pulse wave signal SM whose magnitude $Mh_0$ has exceeded the reference value Mb for the first time at the current BPMC. Step S10 is followed by step S11 at which the temporary maximum blood pressure is displayed on the display 38. In the present embodiment, step S8 stored in the ROM 34, the CPU 30 and RAM 36 for effecting step S8, the cuff 10, pressure sensor 12, pulse-wave discriminator circuit 26 and other members cooperate with each other to serve as the means for continuously detecting the heartbeat-synchronous pulses. Further, steps S9 and S10 stored in the ROM 34 and the CPU 30 and RAM 36 for effecting those steps, serve as the means for comparing with the reference value Mb the varying magnitude of the heartbeat-synchronous pulses detected at the current BPMC and determining the temporary maximum blood pressure based on the comparison result. Moreover, step S11 stored in the ROM 34, the CPU 30 and RAM 36 for executing step S11, and the display 38 cooperate with each other to serve as the means for displaying the temporary maximum blood pressure before determination of proper and more accurate maximum blood pressure at the current BPMC.

At the following step S12 it is judged whether or not cuff pressure P has been decreased below a predetermined target level Pu, which is sufficiently lower than minimum blood pressure of normal people or estimated minimum blood pressure of the subject, for example 30 mmHg. If the judgement at step S12 is negative, step S12 is repeated until the judgement is turned to be affirmative, while pulses of pulse wave signal SM are continuously read in. Meanwhile, once the judgement at step S12 is turned affirmative, step S12 is followed by step S13 at which the reading-in of the pulses of pulse wave signal SM is terminated. At the following step S14 the CPU 30 effects blood pressure determining routine in which proper and more accurate blood pressure is determined based on variation in magnitude of the read-in pulses of pulse wave signal SM, by a well-known "oscillometric method". In the method, the proper maximum blood pressure is determined based on a mean pulse having a maximum signal magnitude (indicated at "a" in the graph of FIG. 3), while minimum blood pressure is determined based on a pulse occurring on the diastolic-pressure side (for example, indicated at "b" in FIG. 3). Accordingly, the proper maximum blood pressure cannot be determined prior to the termination of a whole blood pressure measuring cycle (BPMC), for example before all the pulses of pulse wave signal SM as indicated in the graph of FIG. 3 have been read in. Effecting one BPMC usually takes about 20 seconds.

Step S14 is followed by step S15 at which the determined maximum and minimum blood pressure is displayed on the display 38, and the electromagnetic valve 20 is opened to rapidly deflate the cuff 10 and decrease cuff pressure P. Subsequently the control of the CPU 30 is returned to step S2 to repeat blood pressure measurements.

Back to step S5, if the judgement at step S5 is affirmative, namely, if the current BPMC is an initial one, the control of the CPU 30 goes to step S16 at which cuff pressure P is decreased similar to step S7. Step S16 is followed by step S17 at which pulses of pulse wave signal SM are consecutively read in. Step S17 is followed by steps S12 through S15 to determine maximum and minimum blood pressure and display the determined blood pressure on the display 38.

As is apparent from the foregoing, TMBP of a subject at a current BPMC is determined by utilizing the reference value Mb, which is determined based on a magnitude of a pulse out of pulse wave signal SM (i.e., heartbeat-synchronous pulses) which pulse corresponds to proper and accurate maximum blood pressure of the same subject detected at a preceding BPMC. Thus, in the instant apparatus, considerably reliable TMBP is determined and displayed.

Furthermore, in the instant apparatus, TMBP (temporary maximum blood pressure) is displayed upon detection of a pulse (from currently detected pulse wave signal SM) whose magnitude has exceeded the reference value Mb determined based on a pulse corresponding to the proper maximum blood pressure measured at the preceding BPMC (blood pressure measuring cycle), at each of continuous BPMC's except for an initial one, prior to determination of proper maximum (and minimum) blood pressure at each BPMC. Thus, the TMBP displayed by the instant apparatus is not changed during each BPMC. In this respect, the instant apparatus is contrasted to the conventional one of the type in which TMBP is determined based on a maximum of differences in magnitude each of which is measured between each pair of consecutive pulses of currently detected pulse wave signal SM, and accordingly initial TMBP being displayed may be changed to another value because of detection of another maximum magnitude difference between a pair of consecutive pulses detected after the time of having displayed the initial TMBP.

While in the illustrated embodiment the average of magnitudes of three consecutive pulses SM2, SM3, SM4 in which intermediate pulse SM3 corresponds to the proper maximum blood pressure detected at the preceding BPMC, is used as the reference value Mb, it is possible to utilize as the reference value Mb an average of magnitudes of more than four pulses selected from pulse wave signal SM. Further, for the fourth and following BPMC's, it is possible to determine the reference value Mb by utilizing equation (1) or (2) as follows:

$$Mb = (Mb1 + 2Mb2)/3 \qquad (1)$$

$$Mb = (Mb1 + Mb2)/2 \qquad (2)$$

, wherein

Mb is the reference value for a current BPMC,

Mb1 is the reference value used at the preceding BPMC, and

Mb2 is the reference value used at a BPMC preceding the preceding BPMC.

Thus, according to the principle of the present invention, the reference value Mb to be used for a current BPMC is determined based on at least a pulse out of heartbeat-synchronous pulses detected at a preceding BPMC which pulse corresponds to proper maximum blood pressure determined at the preceding BPMC.

Although in the illustrated embodiment the blood pressure determining routine at step S14 is not effected until all the pulses as indicated in the graph of FIG. 3 have been detected, it is possible to adapt the present apparatus to operate on a real-time basis. In this case, the flow chart of FIG. 4 may be used. The flow chart includes steps SS1 through SS16. In the flow chart, "F=1" means that the reference value Mb has been determined, while "F=0" means that the reference value Mb has not been determined.

While in the illustrated embodiment pulse wave is used as the heartbeat-synchronous pulses, it is possible to utilize other sorts of heartbeat-synchronous pulses than pulse wave, such as pulse sound (Korotkoff sounds) produced as pressure in an inflatable cuff is varied, or oscillation of the wall of an arterial vessel detected by utilizing Doppler effect. In the case of utilizing the Korotkoff sounds, it takes a comparatively long time to execute algorithm for determining maximum and minimum blood pressure. In this case, therefore, it is more advantageous to determine and display temporary maximum blood pressure at early stage in each of continuous blood pressure measuring cycles by the apparatus in accordance with the present invention.

Although in the illustrated embodiment the blood pressure measurement is effected as pressure in the cuff 10 is decreased, it is possible to measure blood pressure as the cuff pressure is increased.

While the present invention has been described in its preferred embodiment with detailed particularities, it is to be understood that the invention may be embodied with various changes, improvements and modifications which may occur to those skilled in the art without departing from the spirit and scope of the invention defined in the appended claims.

What is claimed is:

1. A blood pressure measuring apparatus for continuously measuring blood pressure values of a subject at a plurality of blood pressure measuring cycles, the apparatus comprising:

detecting means for continuously detecting heartbeat-synchronous pulses produced from said subject at each of said measuring cycles, said detecting means including an inflatable cuff to be set around a body portion of said subject, the magnitude of said pulses being varied as pressure in said inflatable cuff is varied at said each measuring cycle, the varying magnitude of said pulses being detected by said detecting means;

selecting means for selecting a pulse from the heartbeat-synchronous pulses detected at a preceding blood pressure measuring cycle, the selected pulse corresponding to a proper maximum blood pressure determined at said preceding blood pressure measuring cycle;

first determining means for determining a reference value based on at least a magnitude of said selected pulse;

second determining means for comparing, with said reference value, the varying magnitude of the heartbeat-synchronous pulses detected at a current blood pressure measuring cycle, and determining as a temporary maximum blood pressure a pressure in said inflatable cuff when the varying magnitude of the currently detected heartbeat-synchronous pulses exceeds said reference value; and display means for displaying said temporary maximum blood pressure before determination of a proper maximum blood pressure at said current blood pressure measuring cycle.

2. The apparatus as set forth in claim 1, wherein said first determining means determines said reference value by obtaining an average of magnitudes of three pulses of the heartbeat-synchronous pulses detected at said preceding blood pressure measuring cycle, said three pulses consisting of an intermediate pulse corresponding to the proper maximum blood pressure determined at said preceding blood pressure measuring cycle, and two pulses preceding and following said intermediate pulse.

3. The apparatus as set forth in claim 1, wherein said first determining means determines said reference value based on the reference value determined at said preceding blood pressure measuring cycle and the reference value determined at a blood pressure measuring cycle preceding said preceding blood pressure measuring cycle.

4. The apparatus as set forth in claim 1, wherein said heartbeat-synchronous pulses consist of pressure oscillations produced in said inflatable cuff synchronously with heartbeat of said subject.

5. The apparatus as set forth in claim 1, wherein said heartbeat-synchronous pulses consist of Korotkoff sounds produced from said body portion of said subject synchronously with heartbeat of the subject.

6. The apparatus as set forth in claim 1, wherein said heartbeat-synchronous pulses are detected as said pressure in said inflatable cuff is decreased.

7. The apparatus as set forth in claim 1, wherein said heartbeat-synchronous pulses are detected as said pressure in said inflatable cuff is increased.

* * * * *